United States Patent
Smith et al.

(10) Patent No.: US 10,660,758 B2
(45) Date of Patent: May 26, 2020

(54) METHOD AND DEVICE FOR REDUCING IMPLANT CONTAMINATION FROM HANDLING

(71) Applicant: Biomet Manufacturing, LLC, Warsaw, IN (US)

(72) Inventors: Daniel B. Smith, Warsaw, IN (US); Katie M. Schindler, Fort Wayne, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 0 days.

(21) Appl. No.: 15/943,089

(22) Filed: Apr. 2, 2018

(65) Prior Publication Data
US 2018/0221154 A1    Aug. 9, 2018

Related U.S. Application Data

(62) Division of application No. 14/182,696, filed on Feb. 18, 2014, now abandoned.

(51) Int. Cl.
*A61F 2/30* (2006.01)
*A61F 2/00* (2006.01)
(Continued)

(52) U.S. Cl.
CPC .............. *A61F 2/30* (2013.01); *A61F 2/0095* (2013.01); *A61F 2/34* (2013.01); *A61F 2/36* (2013.01);
(Continued)

(58) Field of Classification Search
CPC ........ A61F 2/0095; A61F 2/3609; A61F 2/30; A61F 2/34; A61F 2/36; A61F 2/38; A61F 2002/30718
(Continued)

(56) References Cited

U.S. PATENT DOCUMENTS

| | | | |
|---|---|---|---|
| 4,585,453 A * | 4/1986 | Martin ................ | A61F 2/2427 623/2.11 |
| 4,750,619 A * | 6/1988 | Cohen ................ | A61F 2/0095 206/363 |

(Continued)

FOREIGN PATENT DOCUMENTS

| CN | 201692097 U | 1/2011 |
|---|---|---|
| CN | 106102653 A | 11/2016 |

(Continued)

OTHER PUBLICATIONS

"U.S. Appl. No. 14/182,696, Appeal Brief filed Oct. 6, 2016", 19 pgs.
(Continued)

*Primary Examiner* — Rafael A Ortiz
(74) *Attorney, Agent, or Firm* — Schwegman Lundberg & Woessner, P.A.

(57) ABSTRACT

An orthopedic implant has a removable handling cover coupled thereto which includes a thin-walled layer extending over a grasping portion of the outer surface. An outer container can sealingly house the orthopedic implant within a sterile environment and support the orthopedic implant in an orientation that presents the handling cover for grasping. A surgeon can manually grasp, handle and manipulate the implant into an implantation position, and remove the handling cover from the implant during implant surgery, and without the need to directly contact any surface of the orthopedic implant itself. Related methods of providing such an implant assembly and of reducing infection from contamination during implantation surgery are also disclosed.

6 Claims, 6 Drawing Sheets

(51) Int. Cl.
*A61F 2/36* (2006.01)
*A61F 2/38* (2006.01)
*A61F 2/34* (2006.01)

(52) U.S. Cl.
CPC ....... *A61F 2/38* (2013.01); *A61F 2002/30718* (2013.01)

(58) Field of Classification Search
USPC ................ 623/22.13, 23.75; 206/363–366, 206/438–441, 63.3
See application file for complete search history.

(56) References Cited

U.S. PATENT DOCUMENTS

| | | | |
|---|---|---|---|
| 5,061,270 | A | 10/1991 | Aboczky |
| 5,409,492 | A | 4/1995 | Jones et al. |
| 5,756,145 | A | 5/1998 | Darouiche |
| 5,853,745 | A | 12/1998 | Darouiche |
| 5,887,707 | A | 3/1999 | Anascavage et al. |
| 6,432,141 | B1 | 8/2002 | Stocks et al. |
| 6,468,281 | B1 | 10/2002 | Bädorf et al. |
| 6,477,923 | B2 | 11/2002 | Amis |
| 6,810,880 | B1 | 11/2004 | Jennings, Jr. et al. |
| 6,863,692 | B2 * | 3/2005 | Meulink ............... A61F 2/0095 206/363 |
| 7,637,911 | B2 | 12/2009 | Zubok et al. |
| 7,674,292 | B2 | 3/2010 | Zubok et al. |
| 7,806,901 | B2 | 10/2010 | Stad et al. |
| 8,282,649 | B2 | 10/2012 | Long et al. |
| 8,282,651 | B2 | 10/2012 | Ciccone et al. |
| 8,413,811 | B1 | 4/2013 | Arendt |
| 8,465,546 | B2 | 6/2013 | Jodaitis et al. |
| 8,790,413 | B2 * | 7/2014 | Meulink ............... A61F 2/0095 623/23.46 |
| 9,216,087 | B2 * | 12/2015 | Dickerson ............ A61F 2/3607 |
| 2002/0093124 | A1 * | 7/2002 | Wang ........................ A61F 2/30 264/478 |
| 2004/0098134 | A1 | 5/2004 | Meulink |
| 2005/0033430 | A1 | 2/2005 | Powers et al. |
| 2006/0287733 | A1 | 12/2006 | Bonutti |
| 2007/0100464 | A1 | 5/2007 | Meulink |
| 2008/0243135 | A1 | 10/2008 | Robinson |
| 2009/0012529 | A1 | 1/2009 | Blain et al. |
| 2009/0112217 | A1 | 4/2009 | Hester et al. |
| 2010/0016860 | A1 | 1/2010 | Mccardel |
| 2010/0023019 | A1 | 1/2010 | Fuhrer et al. |
| 2010/0063597 | A1 | 3/2010 | Gradel |
| 2011/0098724 | A1 | 4/2011 | Cichocki et al. |
| 2011/0155592 | A1 | 6/2011 | Liccardo et al. |
| 2011/0301612 | A1 | 12/2011 | Richter et al. |
| 2012/0123429 | A1 | 5/2012 | Beedall et al. |
| 2012/0130387 | A1 | 5/2012 | Simpson et al. |
| 2012/0158618 | A1 | 6/2012 | Roskos |
| 2013/0012999 | A1 | 1/2013 | Petit |
| 2013/0018418 | A1 | 1/2013 | Petit |
| 2013/0075267 | A1 | 3/2013 | Shawcross et al. |
| 2015/0230926 | A1 | 8/2015 | Smith et al. |

FOREIGN PATENT DOCUMENTS

| | | | | |
|---|---|---|---|---|
| CN | 109938884 A | | 6/2019 | |
| WO | WO-2012153092 A1 | * | 11/2012 | ........... A61F 2/0095 |
| WO | WO-2012153092 A1 | | 11/2012 | |
| WO | WO-2015126818 A1 | | 8/2015 | |

OTHER PUBLICATIONS

"U.S. Appl. No. 14/182,696, Appeal Decision mailed Feb. 2, 2018", 7 pgs.
"U.S. Appl. No. 14/182,696, Final Office Action dated Jun. 16, 2016", 17 pgs.
"U.S. Appl. No. 14/182,696, Non Final Office Action dated Feb. 1, 2016", 15 pgs.
"U.S. Appl. No. 14/182,696, Reply Brief filed Jan. 23, 2017", 3 pgs.
"U.S. Appl. No. 14/182,696, Response filed Mar. 2, 2016 to Non Final Office Action dated Feb. 1, 2016", 14 pgs.
"U.S. Appl. No. 14/182,696, Response filed Nov. 13, 2015 to Restriction Requirement dated Oct. 7, 2015", 7 pgs.
"U.S. Appl. No. 14/182,696, Restriction Requirement dated Oct. 7, 2015", 9 pgs.
"International Application Serial No. PCT/US2015/016131, International Search Report dated May 15, 2015", 4 pgs.
"International Application Serial No. PCT/US2015/016131, Written Opinion dated May 15, 2015", 7 pgs.
"Chinese Application Serial No. 201580015807.5, Office Action dated May 29, 2018", w/ English translation, 16 pgs.
"Chinese Application Serial No. 201580015807.5, Response filed Aug. 2, 2018 to Office Action dated May 29, 2018", 4 pgs.
"Chinese Application Serial No. 201580015807.5, Decision of Rejection dated Nov. 27, 2018", (W/ English Translation), 16 pgs.
"Chinese Application Serial No. 201580015807.5, Office Action dated May 17, 2017", (W/ English Translation), 17 pgs.
"Chinese Application Serial No. 201580015807.5, Office Action dated Dec. 1, 2017", (W/ English Translation), 17 pgs.
"Chinese Application Serial No. 201580015807.5, Response filed Feb. 13, 2018 to Office Action dated Dec. 1, 2017", (W/ English Translation of Claims).
"Chinese Application Serial No. 201580015807.5, Response filed Aug. 22, 2017 to Office Action dated May 17, 2017", (W/ English Translation of Claims), 10 pgs.
"European Serial No. 15708959.0, Response filed May 8, 2017 to Action dated Oct. 26, 2016", 19 pgs.
"International Application Serial No. PCT/US2015/016131, International Preliminary Report on Patentability dated Sep. 1, 2016", 9 pgs.

* cited by examiner

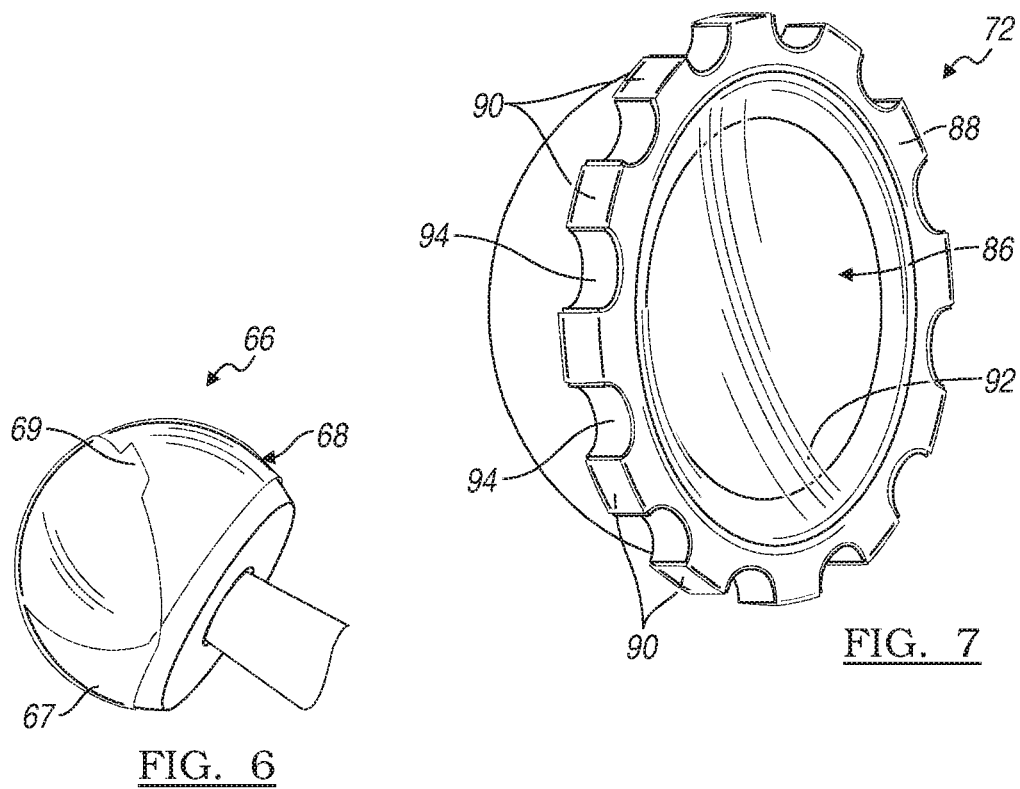
FIG. 6
FIG. 7
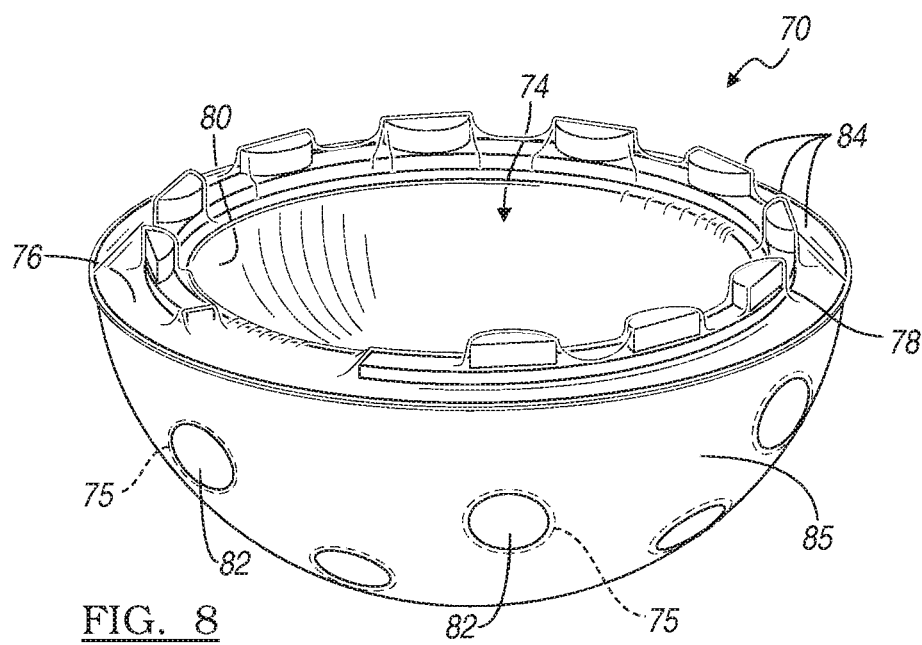
FIG. 8

METHOD AND DEVICE FOR REDUCING IMPLANT CONTAMINATION FROM HANDLING

FIELD

The present disclosure relates to methods and devices for reducing implant contamination from handling.

BACKGROUND

This section provides background information related to the present disclosure which is not necessarily prior art.

Infection remains a devastating complication of total joint replacement, affecting about one to four percent, of all primary procedures. Infection can occur by contamination at the surgical site at the time of the procedure or by hematogenous seeding. Possible routes for contamination at the time of surgery include the surgical team touching the implant or tissues within the operative site with contaminated gloved hands or instruments. Instruments can become contaminated because the cleaning procedures were not adequate after prior use or because the instruments were contaminated during the current surgery.

In a recent study, Davis showed that 63 percent of primary hip and knee arthroplasties had contamination in the field of operation (Davis 1999). Davis' study also showed that about 29 percent of gloves used in the primary hip and knee procedures for preparation were found to be contaminated. In another study, Maathuis showed that 30 percent of broaches used in total hip arthroplasty had bacterial contamination at the end of the procedure (Maathuis 2005).

One significant source of such contamination is when packages containing sterile implantable devices are opened in the operating room, it is almost always necessary to manually remove the implant from the packaging. In many cases, removal of the implant from the package requires handling of the implant with potentially contaminated gloves or implements, which can transfer contamination to the surface of the implant.

SUMMARY

This section provides a general summary of the disclosure, and is not a comprehensive disclosure of its full scope or all of its features.

Disclosed is an orthopedic implant assembly providing reduced contamination from handling that can include an orthopedic implant having an outer surface including a grasping portion and a bone-facing portion. A removable handling cover is coupled to the orthopedic implant and includes a thin-walled layer extending over the grasping portion of the outer surface. An outer container can sealingly house the orthopedic implant within a sterile environment and support the orthopedic implant in an orientation that presents the handling cover for grasping upon opening the outer container. The removable handling cover can provide a removable grasping portion for manually grasping, handling and manipulating the implant into an implantation position with the bone-facing surface facing an adjacent bone during implant surgery without the need to directly contact any of the outer surface of the orthopedic implant. And the removable handling cover can be removable during surgery after the implant is moved into the implantation position.

Also disclosed is a method of providing an orthopedic implant with reduced contamination from handling. The method can include covering a grasping portion of the orthopedic implant with a handling cover comprising a thin-walled, protective layer that is removable from the implant during implantation surgery. The method can also include supporting the orthopedic implant in an orientation within a container that presents the removable, thin-walled, protective layer to a user upon opening the container, and sealing the orthopedic implant in a sterile condition within a sterile environment of a container.

A method of reducing infection from contamination of an orthopedic implant during surgery is additionally disclosed. The method can include opening a sterile container housing the orthopedic implant to present a removable thin-walled layer selectively covering a handling portion of the implant for easy grasping. The method can additionally include handling and manipulating the implant into an implantation position by manually grasping the presented removable thin-walled layer, and removing the removable thin-walled layer prior to closure during the implantation procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is a perspective view of a femoral head component of the hip implant of FIG. 5, including a handling cover.

FIG. 7 is a perspective view of an acetabular component of the hip implant of FIG. 5, including a handling cover.

FIG. 8 is a perspective view of an acetabular liner component of the hip implant of FIG. 5, including a handling cover.

Corresponding reference numerals indicate corresponding parts throughout the several views of the drawings.

DETAILED DESCRIPTION

Example embodiments will now be described more fully with reference to the accompanying drawings.

Figure 1:
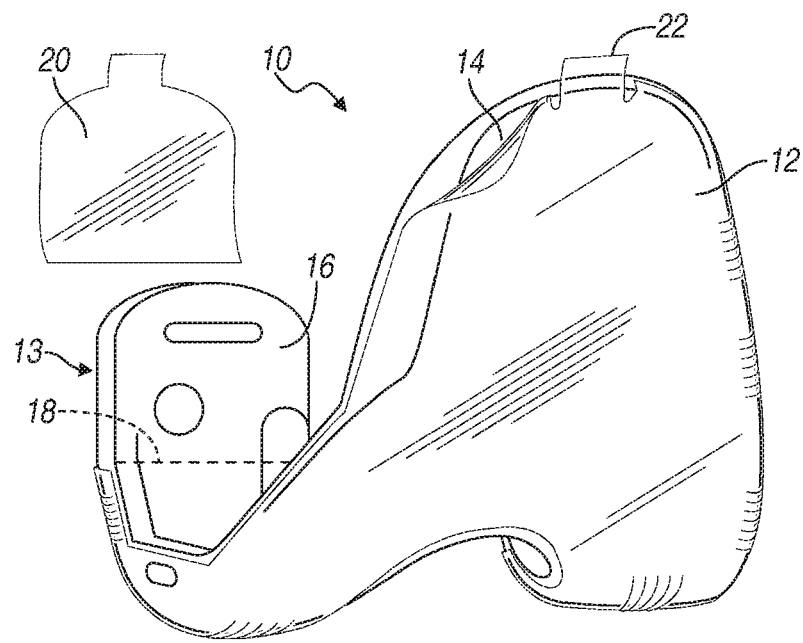
FIG. 1 is a perspective view of a femoral component of a knee implant, including a handling cover.

FIGS. 1-4 illustrate various orthopedic knee implant components that can be used together, each including a handling or grasping cover. Specifically, FIG. 1 illustrates a femoral component 10 of the orthopedic knee implant. The handling cover 12 of the femoral component 10 comprises a compliant film that covers a grasping portion 14 of the outwardly facing surface of the femoral component 10.

In this embodiment, the grasping cover 12 film extends over the grasping portion 14, which is at least a portion of the non-bone facing surface, including the sides of the femoral component 10. Thus, a surgeon can readily grasp, manipulate and place the femoral component 10 into an implantation position with the bone facing surface 16 adjacent the femoral bone while the surgeon only directly contacts or touches the grasping cover 12. In other words, there is no need to directly contact any portion of any surface 14 or 16 of the femoral component 10 during implantation surgery.

A posteriorly-facing portion 13 of the outer surface 14 of the femoral component 10, above dotted line 18 for example, can lack any handling cover 12 film. Alternatively, a secondary portion 20 of the handling cover 12 film above dotted line 18 can be separately removed prior to positioning the femoral component 10 in an implantation position. After the femoral component 10 is in position, the remainder, or primary portion of the handling cover 12 film can be removed from the grasping surface 14 of the femoral component 12.

Figure 3:
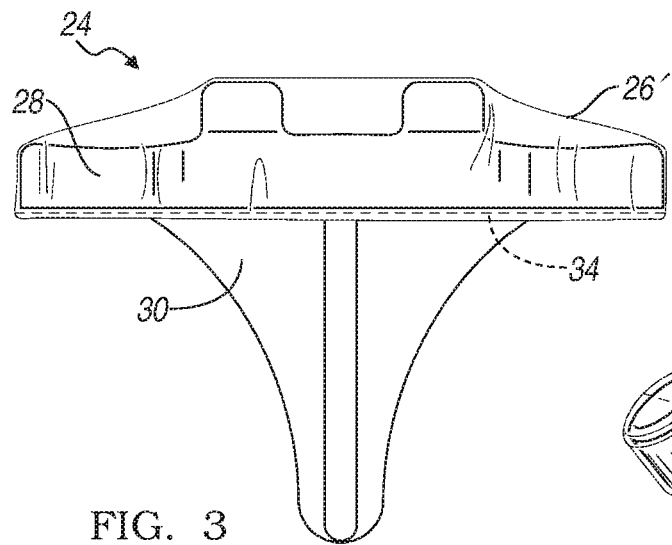
FIG. 3 is a side elevation view of a tibial component of the knee implant of FIG. 2, including an alternative handling cover.

The handling cover 12 film can include a tab 22 which the surgeon can grasp to aid removal of the film 12. The handling cover 12 film can comprise a thin film coated with adhesive to adhere to the grasping surface 14 of the femoral component 10. The handling cover film can comprise a naturally adhering film, for example, held in place with static electricity. The adhered handling cover 12 film can also comprise a shrink wrap film. Other mechanisms can be used to adhere a handling cover 12 film to the implant. For example, an elasticized member 34 at an opening of a thin film member 26' (similar to a shower cap) can be used as illustrated in FIG. 3.

The handling cover 12 film can be formed directly on the implant component. For example, the grasping portion of the femoral component 10 can be coated with a material that forms a film on the surface and that is removable during implantation surgery as described herein. For example, the coating material can be printed or painted on the grasping surface 14 of the femoral component 10 of the implant to form the handling cover 12 film.

Figure 2:
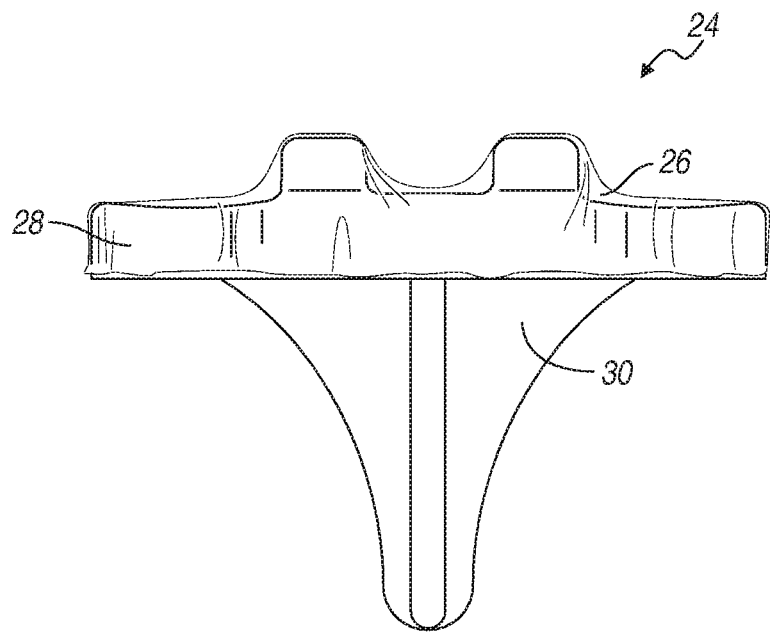
FIG. 2 is a side elevation view of a tibial component of the knee implant of FIG. 1, including a handling cover.

FIG. 2 illustrates a tibial component 24 that can be used with the orthopedic knee implant of FIG. 1. Similar to the discussion above, the tibial component 24 includes a thin-walled handling cover 26 film over a grasping surface 28. In this embodiment, the grasping surface 28 includes the upwardly facing tibial tray and sides. Here too, there is no handling cover 26 on the bone facing surface 30 of the tibial component 24, allowing the tibial component 24 to be grasped and manipulated into an implantation position adjacent the bone without the surgeon needing to directly contact any portion of the tibial component 24. The handling cover 26 film can be removed from the tibial component 24 after it has been moved into an implantation position.

As appropriate, cement can be applied to a bone opposing surface 30 of an implant component, including tibial component 24. The surgeon can grasp and manipulate the tibial implant component 24 using the handling cover 26 film. The handling cover 26 film can also help insure bone cement does not remain on the tibial component 24 in undesired locations. For example, any cement extending onto the handling cover 26 film, can be removed along with removal of the handling cover 26 film.

Figure 4:
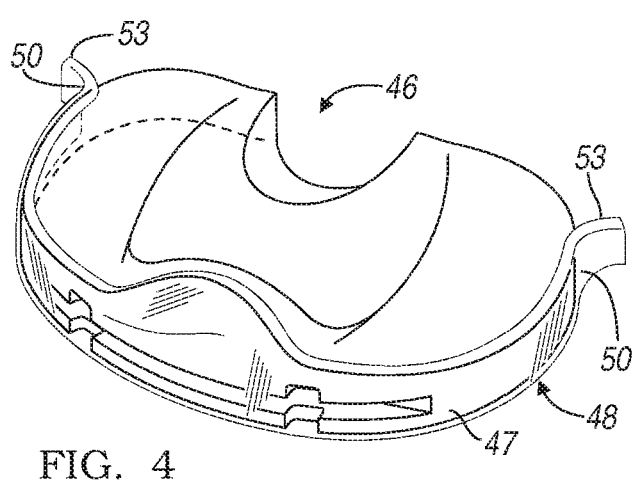
FIG. 4 is a perspective view of another polyethylene component of the knee implant of FIG. 1, including an alternative handling cover.

FIG. 4 illustrates a polyethylene component 46 that can be used with the orthopedic knee implant components of FIGS. 1 and 2 or 3. The polyethylene component 46, includes a handling cover 48. After the handling cover 48 film has been removed from the tibial component 24, the polyethylene component 46 can be coupled to the upper surface or tibial tray thereof, opposing the femoral component 10.

The grasping portion 47 and corresponding handling cover 48 film can include only a portion of the sides thereof. For example, the handling cover 48 film can cover the sides and a few millimeters of the top, bottom, or both. In addition, the handling cover 48 can end at edges 50 so that a posterior portion of the sides of the polyethylene component 46 is left uncovered. In the illustrated embodiment, the handling cover 48 can extend around approximately 270 degrees of the anterior portion of the side wall. In other words, leaving about 45 degrees on either side of the posterior midpoint of the side wall uncovered by the handling cover 48.

In addition, a separate handling cover film (not shown, but similar to 20 of FIG. 1) can be provided over the upper surface of the polyethylene component 46. Thus, the separate handling cover film can provide additional protection, and removed prior to positioning the polyethylene component 46 into an implantation position.

The polyethylene component 46 can be grasped and manipulated into an implantation position via the handling cover 48 film and without the surgeon needing to directly contact with any portion of the polyethylene component 46. A surgeon can grasp extending tabs 53 to peel the handling cover 48 film from the polyethylene component 46 after it is in an implantation position. Extending or grasping tabs 53 can be provided as an extension of the film member itself as illustrated, or as an extending string member (not shown), or as another extending or grasping tab member.

Figure 5:
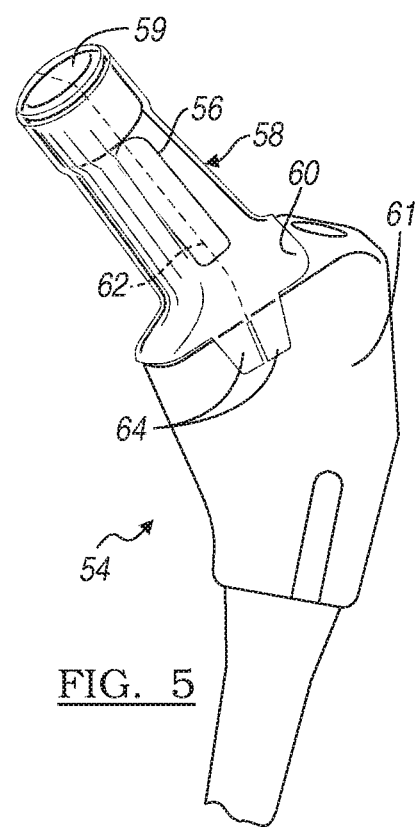
FIG. 5 is a perspective view of a femoral stem component of a hip implant, including a handling cover.

FIGS. 5-8 illustrates various orthopedic hip implant components. FIG. 5 illustrates a femoral stem component 54 of the orthopedic hip implant. A grasping portion 56 can include the trunnion 59, shoulder region 60 and neck therebetween. The grasping portion 56 is covered by a handling cover 58 film. In contrast, the bone facing or opposing portion 61 of the stem component 54 might not include a handling cover 58, or can have a handling cover (not shown) that can be removed prior to manipulating the femoral stem component 54 into an implantation position adjacent the bone by grasping the handling cover 58 film and without directly contacting any surface of the femoral stem component 54.

The handling cover 58 of this embodiment includes a frangible tear line or cut-through line providing a separation line identified by dotted line 62. For example, a surgeon can grasp pulls the extending grasping tabs 64 to remove the handling cover 58 film in portions along separation line indicated by dotted line 62. Thus, the surgeon can peel two halves of the handling cover film 58 from the femoral stem component 54 without directly contacting the femoral stem component 54.

FIG. 6 illustrates a modular femoral head component 66 for use with the femoral stem component 54 of FIG. 5. The thin-walled handling cover 68 film can overlay essentially all of the outer polished surface or grasping portion 67 of the femoral modular head component 66. In this case a grasping tab 69 is illustrated. Any of the previously described grasping tabs (FIGS. 1 and 2), frangible tear lines (FIGS. 3 and 5), strings (FIG. 4 lifting string and FIG. 5 tear string), or combinations thereof, however, can be used. In addition, the thin-walled handling cover 68 can include a plurality of any of the above.

Not only can the handling cover 68 enable a surgeon to manipulate the femoral head component 66 into an implantation position, but the cover 68 can remain on the surface of the femoral head component 66 corresponding to the grasping surface 56 while an impact tool is used to seat the femoral head component 66 onto the stem component 54. In this way, not only is the risk of contamination reduced from direct manual contact by a surgeon's hands, but also from direct contact with an impaction tool (not shown) during the implantation surgery.

FIGS. 7 and 8 illustrate an acetabular cup component 70 and an acetabular liner component 72 of the hip implant of FIG. 5. A handling cover 74 film can be provided over the upper surface 76 of the acetabular cup component 70, including the locking protrusions 78, and the interior spherical concave surface 80. The handling cover 74 film can include cylindrical openings surrounding each of the screw apertures 82 on the interior surface 80 of the cup 70 (simply indicated by dotted lines 75). In this way, the acetabular component 70 can be grasped and manipulated into an implant position, with the porous outer bone-facing or opposing surface 85 adjacent bone, by contacting only the grasping surface 84 covered by the handling cover 74 film. Screws (not shown) can also be inserted through the apertures 82 to fix the acetabular component 70 in place in a full and final implantation position. Thereafter, the handling cover 74 can be removed.

After the handling cover 74 has been removed from the acetabular component 70, the surgeon can grasp and manipulate the acetabular liner component 72 into place within the concavity of the acetabular component 70. Similar to the acetabular component 70, liner 72 can include a handling cover 86 film over the upper surface 88, including the radial outer side surfaces of locking protrusions 90. In this example, the handling cover 86 is stretched between opposite portions of the upper surface 88 to form a generally planar film above the interior spherical concave surface 92. The handling cover 86 film can be absent from the radial outer sides forming locking recesses 94 to enable the acetabular liner 72 to be fully seated within the cup 70 prior to removing the handling cover 86 film during implantation surgery.

Here too, any of the previously described grasping tabs (FIGS. 1 and 2), frangible tear lines (FIGS. 3 and 5), strings (FIG. 4 lifting string and FIG. 5 tear string), or combinations thereof can form part of the thin-walled handling covers 74 and 86 or be provided in addition to the handling covers 74 and 86. In addition, the thin-walled handling covers 74 and 86 can each include a plurality of any of the above.

Figure 9:
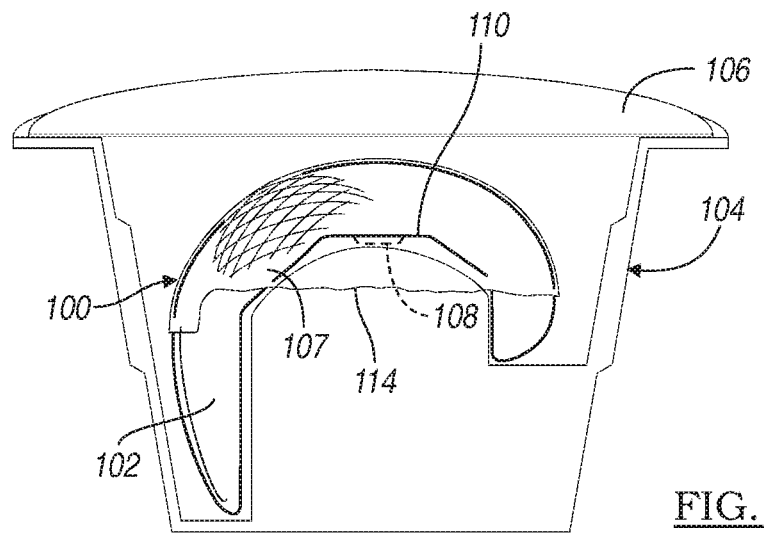
FIG. 9 is a perspective view of a femoral component of a knee implant, including a handling cover, in a sterile package.
Figure 10:
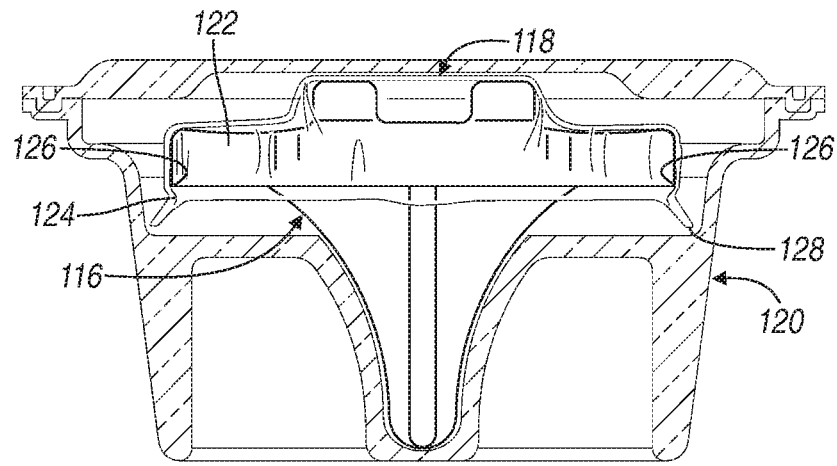
FIG. 10 is a side elevation view of a tibial component of the knee implant of FIG. 9, including a handling cover, in a cross-sectioned sterile package.
Figure 11:
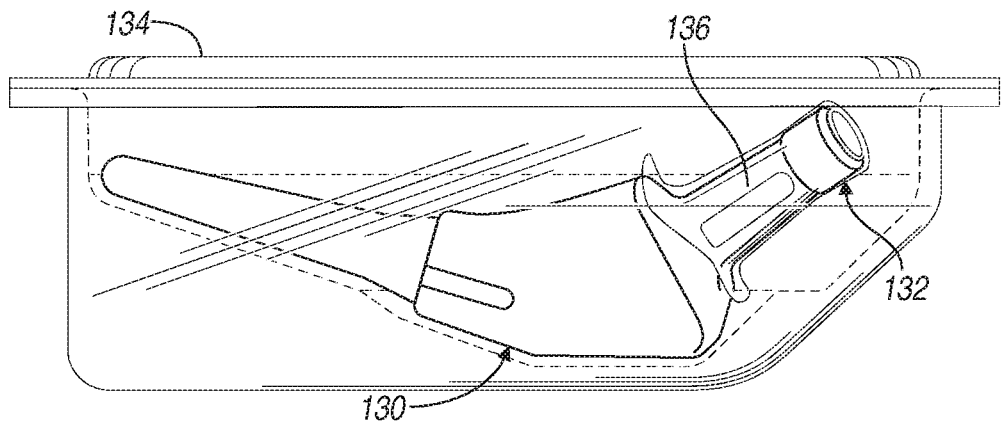
FIG. 11 is a perspective view of a femoral stem component of a hip implant, including a handling cover, in a sterile package.

While each of FIGS. 1-8 illustrate thin-walled grasping covers that all comprise flexible, compliant, or conformable films, FIGS. 9-11 illustrate grasping covers that all comprise thin-walled molded members. It is further noted that each of the embodiments of FIGS. 1-8 can be housed within a sterile environment of a container as specifically illustrated in FIGS. 9-11.

Figure 9A:
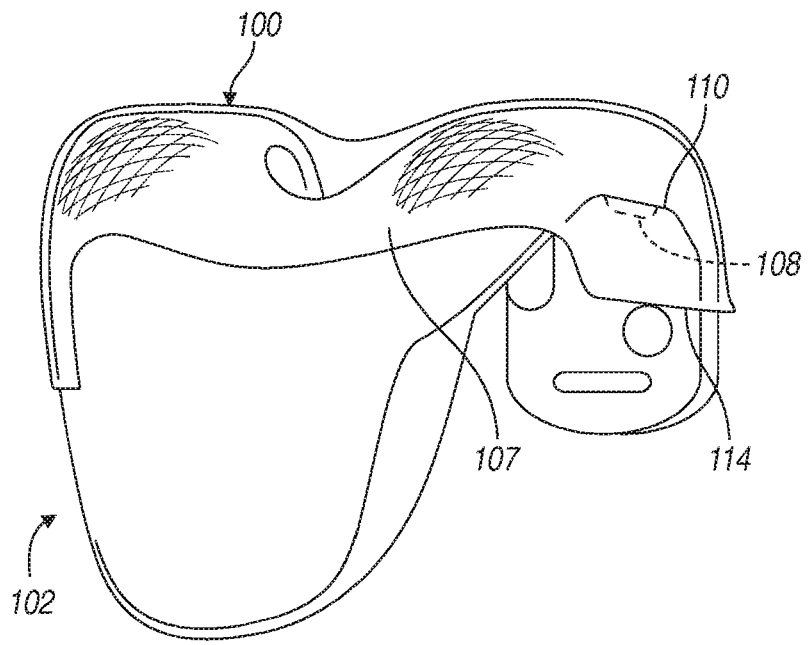
FIG. 9A is a perspective view of the femoral component and handling cover of FIG. 9.

FIGS. 9 and 9A illustrate a molded thin-walled handling cover 100 for a femoral knee implant component 102. The combined assembly 100 and 102 is supported within a sterile container 104 to present the thin-walled molded handling cover 100 to a surgeon upon opening the top cover 106 of the container. Thus, the surgeon can readily grasp and remove the femoral component 102 and handle and manipulate it into an implantation position by grasping the handling cover 100 over the grasping surface portion 107 of the femoral component 102 without directly touching any surface of the actual implant.

The handling cover 100 includes a pair of protrusions 108 on inner surfaces that engage against lower edges 110 on each side of the femoral component 102. Thus, after the surgeon is done manipulating the femoral component 102, pressure can be applied by the surgeon along edges 114 to release the protrusions 108 from the edges 110; facilitating removal of the handling cover 100 from the femoral component 102.

FIG. 10 illustrates a tibial knee implant component 116 which can be used with the component of FIG. 9, and includes a molded thin-walled handling cover 118, in a sterile package 120. Similar to the above, the sterile package 120 supports the tibial component 116 in an orientation that presents the grasping surface 122 covered by the handling cover 118 to the surgeon upon opening the package 120.

The handling cover 118 can include one or more discrete projections or edges 124 that engage an edge 126 of the tibial component 116. Similar to edge 114 of FIGS. 9 and 9A, the handling cover 118 can include a flared portion or tab 128 or can including an edge that can be pushed to release the handling cover projections 124 from the edge 126 of the tibial component 116; facilitating removal of the handling cover 118.

Figure 14:
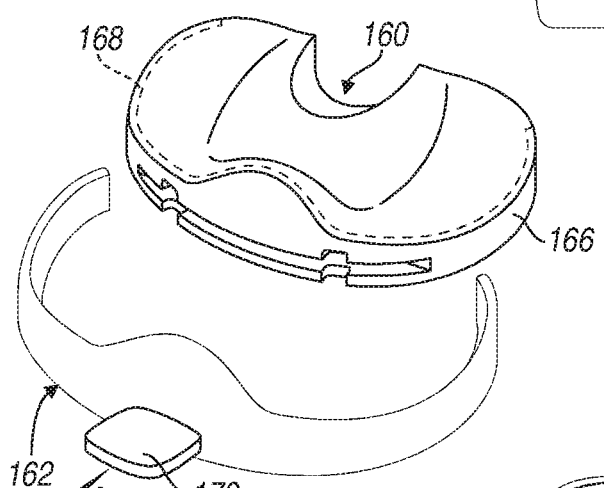
FIG. 14 is a perspective view of a polyethylene component of the knee implant of FIGS. 9 and 10, including a spring member handling cover.

FIG. 14 illustrates a polyethylene knee implant component 160 that can be used with the knee implant components of FIGS. 9 and 10. A molded thin-walled handling cover 162 is formed to extend over a portion of the side wall defining a grasping surface 166. The handling cover 162 can also extend along a periphery of the upper surface indicated by dotted line 168 to help minimize any direct contact with the surface of the polyethylene component 160 during, grasping, handling, and manipulation thereof. The handling cover 162 can be molded as a spring-like member which grasps the sides 166 of the polyethylene component 160, but can also be readily removed during implantation surgery after it has been placed in an implantation position. For example, a surgeon can simply grasp tab 170 and pull in the direction indicated by arrow A, causing spring-like handling cover 162 to be removed from the polyethylene component 160.

Figure 11A:
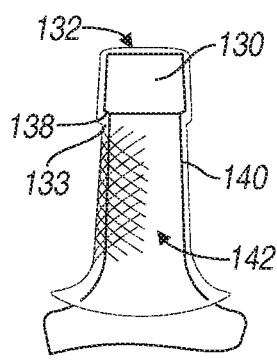
FIG. 11A is a partial axial cross sectional view of a trunnion and shoulder portion of the femoral stem component, including the handling cover, of FIG. 11.
Figure 11B:
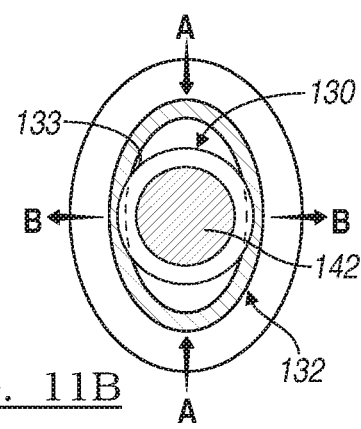
FIG. 11B is a partial transverse cross sectional view of the trunnion of the femoral stem component, including the handling cover, of FIG. 11.

FIGS. 11, 11A, and 11B illustrate a femoral stem component 130 of a hip implant, including a handling cover 132. The femoral stem component 130 is supported in a sterile package 134 to present the grasping surface 136 covered by the handling cover 132 to the surgeon upon opening the container 134 similar to that described above. The handling cover 132 is molded with protrusions 133 to engage the undercut 138 provided by the flats 140 of the neck 142 of the femoral stem component 130.

As best seen in FIG. 11B, the handling cover 132 has an oval cross-sectional shape and is molded from a resilient material. Thus, a surgeon can squeeze along the major axis as indicated by arrows A of the oval cross sectional shape of the handling cover 132; causing expansion along the minor axis as indicated by arrows B to allow the protrusions 133 to move past the projection or edge resulting from the undercut 138 creating the flats 140. In this way, a surgeon can release and remove the handling cover 132 from the femoral stem component 130 after it has been manipulated into an implantation position within the body.

Figure 12:
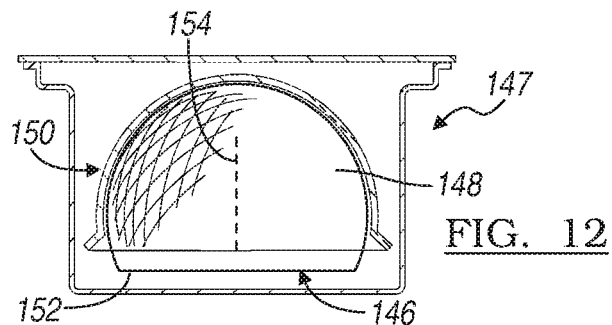
FIG. 12 is a side elevation view of a femoral head component of the hip implant of FIG. 11, including a cross-sectioned handling cover and sterile package.

FIG. 12 illustrates a femoral head component 146 of the hip implant of FIG. 11 within a sterile package 147 supported in an orientation to present the grasping surface 148 covered by a molded thin-walled handling cover 150 to the surgeon upon opening the package 147.

The handling cover 150 can be molded to closely fit the polished outer surface 148 so it is coupled to the head 146 as a result of the reduced diameter adjacent the base 152 of the head 146. Handling cover 150 can include a plurality of split lines indicated by dashed line 154. For example, two, four, six, or some other number of equally spaced split lines 154 can extend partially up from the bottom edge toward the midpoint of the handling cover 150. Thus, the split lines 154 can separate and allow the molded handling cover 150 to be removed from the head 146.

Figure 13:
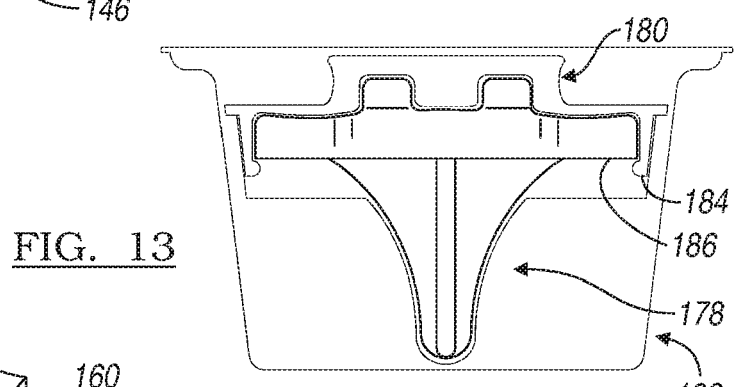
FIG. 13 is a side elevation view of a tibial component of a knee implant with a sterile package that also comprises a portion of the thin-walled handling cover.

FIG. 13 illustrates an alternative tibial component 178, handling cover 180, and sterile container 182. In this example, the handling cover 180 is a molded thin-walled member coupled to the tibial component 178 via a protrusion 184 engaging against the edge 186 of the implant 178. Although a single blister container is illustrated, the sterile container of this or any other embodiment can comprise two or more nested blisters to provide increased assurance of sterility.

Figure 15:
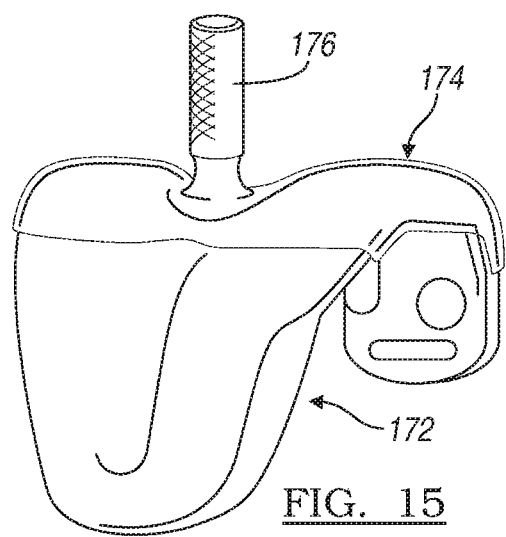
FIG. 15 is a perspective view of a femoral component for a knee implant including a handling cover with an extending handle.

FIG. 15 illustrates a femoral component 172 for a knee implant including a thin-walled handling cover 174 with an extending grasping handle 176. As with the packages and the other features associated with the thin-walled handling covers described herein, such a grasping handle 176 extending from the thin-walled portion of the handling cover 174 can be provided with any of the embodiments described herein, and can be integrally molded with the molded embodiments.

Any of the thin film covers described herein can have a visual appearance that makes it immediately apparent that the thin film cover has not been removed from the implant. For example, the thin film cover can comprise a bright color, a printed pattern, or both, causing the thin film cover to visibly stand out against the implant.

It should further be understood from the above that several orthopedic implant components can be implanted together during a single implantation surgery, and that each one of the components implanted together can be provided as part of an assembly with a thin-walled handling cover, an outer package providing a sterile enclosure, or both.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. For example, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The term "implantation position" can encompass the full and final implantation position of the implant within the body, but is not limited to such. Thus, the term "implantation position" can include other positions, such as where a bone opposing surface of an implant is positioned adjacent a corresponding bone, e.g., in a position near the full and final implantation position.

What is claimed is:

1. A tibial component assembly providing reduced contamination from handling, the assembly comprising:
   a tibial component including a grasping portion;
   a molded, resilient handling cover extending over the grasping portion of the tibial component and removable from the tibial component, the tibial component being manipulatable into an implantation position when grasped by the handling cover over the grasping portion without directly touching any surface of the tibial component, the handling cover including a discrete projection that engages a corresponding edge of the tibial component; and
   a sterile package supporting the handling cover and the tibial component, such that when the sterile package is opened, the handling cover and the tibial component are removable, together, from the sterile package by grasping the handling cover over the grasping portion without directly touching any surface of the tibial component.

2. The assembly of claim 1, wherein the handling cover includes at least one of a flared portion, tab or edge, which, when depressed, releases the discrete projection of the handling cover from the corresponding edge of the tibial component and facilitates removal of the handling cover from the tibial component.

3. The assembly of claim 1, wherein the sterile package comprises:
   a container supporting the handling cover and the tibial component; and
   a top cover sterilely sealing the handling cover and the tibial component inside the container, such that when the top cover is removed from the container, the handling cover and the tibial component are accessible through a top of the container and are removable, together, from the container.

4. A femoral stem component assembly providing reduced contamination from handling, the assembly comprising:
   a femoral stem component including a grasping portion;
   a molded, resilient handling cover extending over the grasping portion of the femoral stem component and removable from the femoral stem component, the femoral stem component being manipulatable into an implantation position when grasped by the handling cover over the grasping portion without directly touching any surface of the femoral stem component, the handling cover including a plurality of protrusions that engage an undercut provided by flats of a neck of the femoral stem component; and a sterile package supporting the handling cover and the femoral stem component such that when the sterile package is opened, the handling cover and the femoral stem component are removable, together, from the sterile package by grasping the handling cover over the grasping portion without directly touching any surface of the femoral stem component.

5. The assembly of claim 4, wherein the handling cover has an oval cross-sectional shape and is molded from a resilient material, such that squeezing the handling cover along a major axis of the oval expands the handling cover along a minor axis of the oval and allows the plurality of protrusions to move past an edge resulting from the undercut and facilitates removal of the handling cover from the femoral stem component.

6. The assembly of claim 4, wherein the sterile package comprises:
   a container supporting the handling cover and the femoral stem component; and
   a top cover sterilely sealing the handling cover and the femoral stem component inside the container, such that when the top cover is removed from the container, the handling cover and the femoral component are accessible through a top of the container and are removable, together, from the container.

* * * * *